United States Patent [19]

Hölscher

[11] Patent Number: 4,911,819

[45] Date of Patent: Mar. 27, 1990

[54] ELECTROCHEMICAL MEASURING CELL HAVING A COMPENSATING MEMBRANE

[75] Inventor: Uvo Hölscher, Stockelsdorf, Fed. Rep. of Germany

[73] Assignee: Drägerwerk Aktiengesellschaft, Lübeck, Fed. Rep. of Germany

[21] Appl. No.: 369,138

[22] Filed: Jun. 21, 1989

[30] Foreign Application Priority Data

Jun. 21, 1988 [DE] Fed. Rep. of Germany ....... 3820841

[51] Int. Cl.⁴ ............................................. G01N 27/30
[52] U.S. Cl. ..................................... 204/408; 204/415
[58] Field of Search .......................... 204/408, 415, 1 P

[56] References Cited

U.S. PATENT DOCUMENTS 3,655,546  4/1972  Marovich et al. .................. 204/415
4,126,531 11/1978  Porter et al. ....................... 204/408

Primary Examiner—G. L. Kaplan
Attorney, Agent, or Firm—Walter Ottesen

[57] ABSTRACT

The invention is directed to a measuring cell for detecting a component of a measuring sample. The measuring cell includes a housing in which an electrolyte as well as a measuring electrode and a counter electrode are accommodated. A membrane separates the electrolyte from the measuring sample and is pressed by a supporting part against the measuring surface of the measuring electrode. This membrane is improved such that it can compensate for volumetric changes in the electrolyte chamber in the clamped condition. The measuring cell is further improved in that a small amount of readiness energy is required for the operational-ready condition and the attachment of the membrane is not critical for its later function. A first portion of this membrane is pressed against the measuring electrode. In the region outside of this first portion and extending up to the peripheral edge where it is attached, a compensating membrane portion is formed which can change in its configuration.

7 Claims, 2 Drawing Sheets

ELECTROCHEMICAL MEASURING CELL HAVING A COMPENSATING MEMBRANE

FIELD OF THE INVENTION

The invention relates to an electrochemical measuring cell for detecting a component in a measuring sample. The measuring cell includes a housing having an electrolyte chamber in which a measuring electrode and a counter electrode are mounted. The electrolyte chamber is partitioned from the measuring sample by means of a membrane which is impermeable to electrolytes and is permeable for the component of the measuring sample. The membrane is pressed by a supporting part onto the measuring surface of the measuring electrode whereby an intermediate chamber is provided between the measuring surface and the membrane which remains constant and is filled with the electrolyte. The supporting part is permeable to the component of the measuring sample.

BACKGROUND OF THE INVENTION

A measuring cell of the kind described above is disclosed in U.S. Pat. No. 3,655,546 incorporated herein by reference. In this measuring cell, the measuring electrode is brought up to the membrane which, in turn, is tightly held by means of an O-ring and a threaded unit so as to lie upon the measuring surface of the measuring electrode. An electrolyte film is formed between the membrane and the measuring surface of the measuring electrode which communicates with the electrolyte in the electrolyte chamber. A counter electrode is mounted in the electrolyte chamber. A perforated plate or supporting grid tightly holds that portion of the membrane in position which lies on the measuring surface of the measuring electrode. This supporting grid is intended, for example, to prevent an overpressure developing within the electrolyte from changing the spacing between the membrane and the measuring surface. Such an overpressure can, for example, develop when the measuring cell is subjected to an underpressure. Another reason for the overpressure in the electrolyte is the formation of bubbles during the measuring operation. A change of the electrolyte layer between the membrane and the measuring electrode would introduce a change in the measuring characteristics of the electrochemical measuring cell.

The disadvantage of the known arrangement of the individual parts of the electrochemical measuring cell is that care must be taken to place the membrane cleanly and tightly on the measuring surface of the measuring electrode. The same degree of care must be taken in the work procedure of tensioning the membrane. In the covered condition, the portions of the membrane outside of that portion which is pressed against the measuring surface are subjected, without protection, to the overpressures which can possibly develop in the electrolyte chamber. The pressure forces which are thereby developed can at least partially bulge the membrane and even perforate the same. During transport, acceleration forces can act on the electrolyte which can operate on the unprotected part of the membrane and cause this part to tear. Volume changes of the electrolyte caused by temperature influences, gas formation, fluid absorption or drying cannot be compensated for by the membrane.

SUMMARY OF THE INVENTION

It is an object of the invention to provide an electrochemical measuring cell of the kind described above which is improved such that it can be fitted with a membrane during production which is not critical for its later function. It is another object of the invention to provide such an electrochemical cell which is ready for operation in the presence of minimal consumption and wherein the membrane clamped in place can compensate for volume changes and pressure increases in the electrolyte chamber.

The electrochemical measuring cell of the invention detects a component contained in a measuring sample. The measuring cell includes: a measuring cell housing defining an electrolyte chamber for accommodating an electrolyte therein; a measuring electrode and a counter electrode arranged in the chamber; a membrane for partitioning the electrolyte chamber from the measuring sample, the membrane being impermeable to the electrolyte and being permeable to the component of the measuring sample; the measuring electrode having a measuring surface facing toward the membrane; a supporting part for accommodating the measuring sample therein and defining a pressing surface for pressing a first portion of the membrane against the measuring surface thereby generating a constant intermediate space filled with electrolyte between the first portion and the measuring surface; passage means formed in the supporting part for permitting access of the measuring sample to the membrane at the first portion thereof; the membrane having a peripheral edge attached to the housing and the region of the membrane outside of the first portion and extending from the measuring surface to the peripheral edge being a second portion of the membrane; and, the second portion of the membrane being a compensating membrane portion formed so as to be changeable in its configuration between the measuring surface and the peripheral edge.

Thus, according to a feature of the invention, the membrane is configured to have a compensating membrane portion which can change in its configuration in the region extending from just outside of the first portion of the membrane where pressure is applied and up to its peripheral edge at which it is attached to the housing of the cell.

The advantage of the invention is essentially seen in that the membrane can compensate for pressure and volume changes in the region outside of the press-on or first portion where pressure is applied thereto. The foregoing notwithstanding, the electrolyte layer disposed beneath the applied pressure is maintained between the supporting part and the measuring surface of the measuring electrode. Electrolyte losses because of vaporization in the gas chamber are balanced by a corresponding reduction of the electrolyte chamber and compensation of the loss. The formation of bubbles in the electrolyte also does not occur which in the known measuring cell is alleviated by providing a larger electrolyte volume. Accordingly, a smaller electrolyte volume is adequate in the measuring cell according to the invention. In this way, the size of the measuring cell is further reduced. The integration of a compensating membrane as part of the measuring membrane makes it unnecessary to compensate for pressure in the electrolyte chamber by means of a separate compensating membrane operatively connected to the latter.

During production of the measuring cell, the membrane does not have to be brought into a defined constant spacing with respect to the measuring surface by means of careful production steps; instead, the membrane is relaxed when clamped to partition the electrolyte chamber from the ambient. The thin electrolyte layer between membrane and measuring surface which is needed for measurement is only generated with the subsequent application of pressure by the supporting part.

Since the thin electrolyte layer between the measuring membrane and the measuring surface of the measuring electrode is only necessary during the measurement, the membrane can remain loosely tensioned over the electrolyte chamber in operational readiness and be at a wide spacing with respect to the measuring surface so that the measuring surface of the measuring electrode is enclosed by a thicker electrolyte layer. In the condition of operational readiness, the measuring and counter electrodes can then be placed electrically in measurement readiness. Because of the large electrolyte layer between membrane and measuring surface, a current flows which is so low that the electrolyte is hardly consumed in the operational-ready condition. Nevertheless, the polarization condition necessary for a measurement is already formed. When applying the supporting part against the membrane, the electrolyte layer reduces to the desired thin electrolyte film whereby the necessary measuring current is simultaneously adjusted and the measuring cell is brought directly into measurement readiness without having to wait for a longer start-up time to pass.

The membrane is preferably so configured that its surface expansion is larger than is at least necessary for partitioning the electrolytic chamber from the measuring sample. By clamping the membrane at the peripheral edge, the membrane can then bulge away from the electrolyte chamber with the opening of the electrolyte chamber nonetheless being sealed off. The intermediate space disposed between the membrane and the measuring surface and filled with electrolyte and necessary for operation is made possible by the bulging of the membrane. When the supporting part is later applied to the membrane, the bulging is eliminated in the region of the measuring surface so that there is still adequate membrane material available to form the compensating membrane portion.

An especially advantageous configuration of the membrane is obtained by configuring the compensating membrane portion as a preformed membrane portion arranged around the measuring surface. The preformed membrane portion can, for example, have a corrugated shape. The corrugated zone can be already formed in the membrane during the production thereof while the membrane portion to be pressed against the measuring surface can have a smooth surface.

The housing of the measuring cell can be accommodated in a supporting housing for the purpose of providing an especially advantageous support of the membrane. This supporting housing contains the supporting part which is subjected to the measuring sample and which is permeable for the component of the measuring sample. The supporting part tightly holds the membrane against the measuring surface under the pressure of spring means. In this way, the measuring cell which was previously held in the operationally-ready condition can be brought into the measuring condition in a simple manner in that the measuring cell housing is inserted into the supporting housing.

It is advantageous to configure the housing of the measuring cell so as to be movable relative to the supporting housing with the spring force being generated by springs engaging between the measuring cell housing and the supporting housing and so as to cause the supporting part to move toward the measuring electrode.

Preferably, the supporting part is so configured that an ancillary chamber is formed between it and the supporting housing which is fillable with a fluid. The fluid preferably contains such components which can diffuse into the electrolyte through the membrane and especially through the compensating membrane portion in order to compensate for a drying up of the electrolyte during a measuring period which extends over a considerable time. As a rule, the electrolytes comprise an aqueous solution so that the fluid can preferably be gelatinized water.

An especially advantageous configuration is provided in that the supporting part comprises an insert extending from the measuring sample opening in the supporting housing up to the measuring surface and which is perforated at that portion thereof which lies against the measuring surface. The insert presses the membrane against the measuring surface and facilitates a passage of the measuring sample through the perforated portion of the insert to the measuring electrode. The remaining impermeable wall portions of the insert separate the ancillary chamber as well as the membrane and the electrolytes from the measuring sample.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
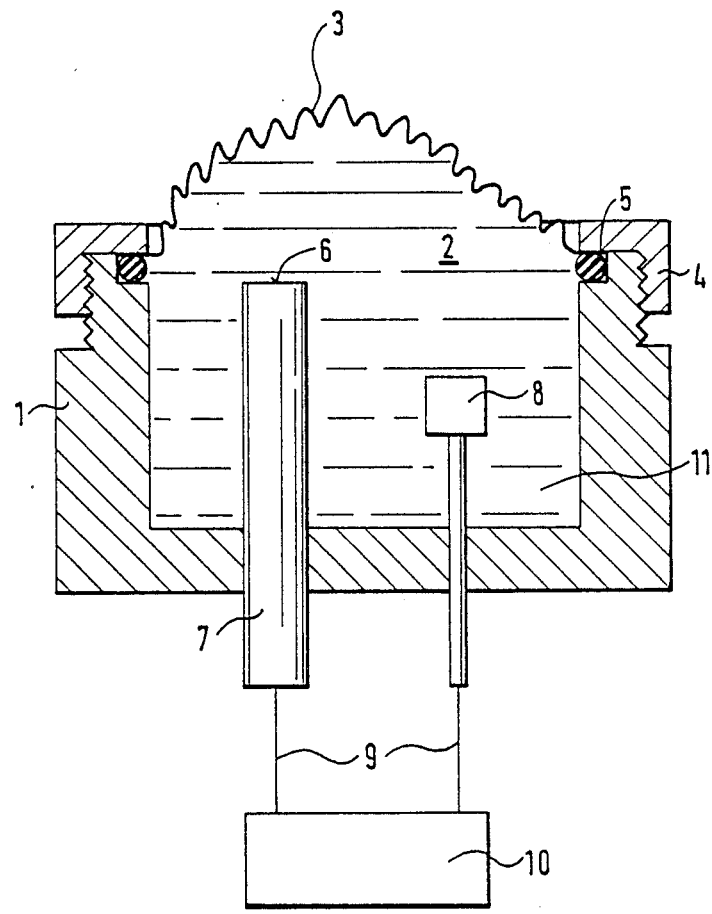
FIG. 1 is a section view taken through measuring cell of the invention in the operational-ready condition; and, FIG. 2 is a section view taken through a measuring cell equipped with a supporting housing and shown in the measuring condition.

FIG. 1 shows a section view of an electrochemical measuring cell according to the invention which includes a housing 1 accommodating the electrolyte 2. The electrolyte 2 is separated from the ambient by a membrane 3 which is impermeable to the electrolyte and, however, permeable with respect to the measuring sample. The housing 1 has a threaded collar 4 which clamps the peripheral edge of the membrane 3 via an O-ring 5. The membrane 3 itself encloses the electrolyte 2 in a loose convex cover so that an adequate quantity of electrolyte is present between the membrane 3 and the measuring surface 6 of the measuring electrode 7. The measuring electrode 7 and the counter electrode 8 are passed through the housing and are connected via measuring connections 9 to a measuring unit 10.

Figure 2:
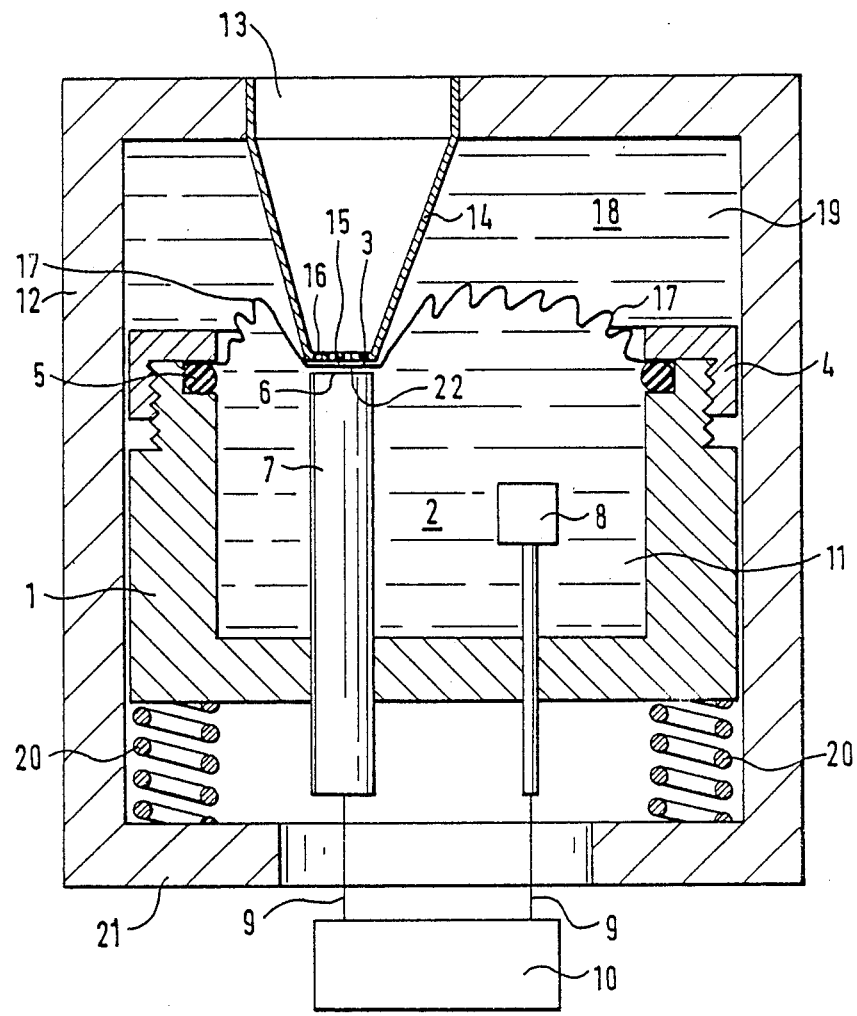

In FIG. 2, the measuring cell shown in FIG. 1 is accommodated in a supporting housing 12. The component parts which correspond to those in FIG. 1 are again identified with the same reference numerals. The measuring sample opening 13 of the supporting housing 12 to the ambient has an insert 14 in the form of a supporting part which has a surface configured as a truncated cone whose smaller end face defines the contact surface 15 which, in its form, is adapted to the measuring surface 6 of the measuring electrode 7. The insert 14 contains perforations 16 to permit access of the measuring sample to the membrane 3 pressed against the measuring surface 6. The press-on portion 22 of the membrane 3 lies between the contact surface 15 and the measuring surface 6. A compensating membrane portion 17 is formed outside of the press-on portion 22 and extends up to the attachment edge of the membrane which is clamped between the collar 4 and the corresponding O-ring 5. This compensating membrane portion 17 constitutes the partitioning surface between the electrolyte 2 and a fluid 18 such as gelatinized water. The fluid 18 fills the ancillary chamber 19 disposed between the supporting housing 12 and the insert 14. Two pressure springs 20 are provided for generating and maintaining the force on the press-on portion 22. These pressure springs 20 engage between the base of the housing 1 and a shoulder 21 of the supporting housing 12.

A thin electrolytic film from the electrolyte 2 remains between the measuring surface 6 and the clamped press-on portion 22 of the membrane 3. This thin electrolytic film is held constant with respect to its thickness against the contact surface 15 by the pressing force of the springs 20. Pressure differences which can possibly occur in the electrolyte 2 with respect to the ambient are taken up by the compensating membrane portion 17.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting a component contained in a measuring sample, the measuring cell comprising:
    a measuring cell housing defining an electrolyte chamber for accommodating an electrolyte therein;
    a measuring electrode and a counter electrode arranged in said chamber;
    a membrane for partitioning said electrolyte chamber from the measuring sample, said membrane being impermeable to said electrolyte and being permeable to the component of the measuring sample;
    said measuring electrode having a measuring surface facing toward said membrane;
    a supporting part for accommodating the measuring sample therein and defining a pressing surface for pressing a first portion on said membrane against said measuring surface thereby generating a constant intermediate space filled with electrolyte between said first portion and said measuring surface;
    passage means formed in said supporting part for permitting access of the measuring sample to said membrane at said first portion thereof;
    said membrane having a peripheral edge attached to said housing and the region of said membrane outside of said first portion and extending from said measuring surface to said peripheral edge being a second portion of said membrane;
    said second portion of said membrane being a compensating membrane portion formed so as to be changeable in its configuration between said measuring surface and said peripheral edge;
    a supporting housing for accommodating said measuring cell housing therein and said supporting part being mounted on said supporting housing; and,
    resilient biasing means operatively connected to said supporting part so as to cause the latter to hold said membrane against said measuring surface of said measuring electrode.

2. The electrochemical measuring cell of claim 1, wherein said compensating membrane portion is formed in that said membrane has a surface expansion greater than is required for partitioning said electrolyte chamber from the measuring sample.

3. The electrochemical measuring cell of claim 1, wherein said compensating membrane portion is configured as a preformed membrane portion arranged in surrounding relationship to said measuring surface of said measuring electrode.

4. The electrochemical measuring cell of claim 1, said measuring electrode being rigidly connected to said measuring cell housing; said measuring cell housing being mounted in said supporting housing so as to be movable relative thereto; and, said resilient biasing means being spring means interposed between said housings so as to cause said supporting part to be pressed against said membrane.

5. The electrochemical measuring cell of claim 1, supporting housing and said membrane conjointly defining an ancillary chamber for accommodating a fluid therein.

6. The electrochemical measuring cell of claim 5, said fluid being gelatinized water.

7. The electrochemical measuring cell of claim 4, said supporting housing having an opening formed therein through which the measuring sample is passed; said supporting part being an insert mounted at sad opening for receiving the measuring sample; said insert extending from said opening to said first portion of said membrane above said measuring surface; and, said passage means being a plurality of perforations formed at least in said pressing surface of said insert.

* * * * *

UNITED STATES PATENT AND TRADEMARK OFFICE
CERTIFICATE OF CORRECTION

PATENT NO. : 4,911,819

DATED : March 27, 1990

INVENTOR(S) : Uvo Hölscher

It is certified that error appears in the above-identified patent and that said Letters Patent is hereby corrected as shown below:

In column 4, line 37: insert -- a -- between "through" and "measuring".

In column 4, line 58: insert -- 1 -- after "housing".

In column 5, line 50: delete "on" and substitute -- of -- therefor.

In column 6, line 38: insert -- said -- after "claim 1,".

In column 6, line 47: delete "sad" and substitute -- said -- therefor.

Signed and Sealed this

Twenty-fifth Day of June, 1991

Attest:

HARRY F. MANBECK, JR.

Attesting Officer

Commissioner of Patents and Trademarks